United States Patent [19]

Milne et al.

[11] Patent Number: 5,017,007

[45] Date of Patent: May 21, 1991

[54] APPARATUS AND MICROBASE FOR SURFACE-ENHANCED RAMAN SPECTROSCOPY SYSTEM AND METHOD FOR PRODUCING SAME

[76] Inventors: Christopher G. Milne, #170 4831 E. Summitt Cr., Knoxville, Tenn. 37919; Paulus P. Shelby, Jr., 3115 B Marion Dr., Knoxville, Tenn. 37918; David L. Bailey, 3700 Sutherland Ave., Apt. Y-3, Knoxville, Tenn. 37919

[21] Appl. No.: 386,564

[22] Filed: Jul. 27, 1989

[51] Int. Cl.$^5$ .............................................. G01J 3/44
[52] U.S. Cl. .................................................. 356/301
[58] Field of Search .................. 356/301, 36, 38, 244

[56] References Cited

U.S. PATENT DOCUMENTS

| | | | |
|---|---|---|---|
| 3,512,876 | 5/1970 | Marks | 356/267 |
| 4,620,284 | 10/1986 | Schnell et al. | 356/301 |
| 4,674,878 | 6/1987 | Vo-Dinh | 356/301 |
| 4,781,458 | 11/1988 | Angel et al. | 356/301 |

OTHER PUBLICATIONS

Bloemer et al., "Surface Electromagnetic Modes in Prolate Spheroids of Gold, Aluminum and Copper", J. Opt. Soc. Am., vol. 5, #12, 12188, pp. 2552-2559.
Vo-Dinh et al., "Surface-Enhanced Roman Spectroscopy for Trace Organic Analysis", Analytical Chemistry, vol. 56, #9, 8/84, pp. 1667-1670.

Primary Examiner—F. L. Evans
Assistant Examiner—K.P. Hantis
Attorney, Agent, or Firm—Neil F. Markva

[57] ABSTRACT

A surface-enhanced Raman spectroscopy (SERS) assembly comprises a radiant energy source for directing a beam of radiant energy toward a target microbase. The target microbase includes a substrate, a roughened surface layer contiguously disposed on the substrate, and a sample-adsorption surface layer contiguously disposed on the first roughened layer. The sample-adsorption surface layer is effective to enhance a scattered Raman signal intensity for adsorbates adjacent the sample-adsorption surface layer by a factor of greater than $10^6$ times. The sample-adsorption surface includes a plurality of submicron needles having a length of at least 3500 angstroms and a width of at least 500 angstroms. A method for manufacturing the target microbase comprises the steps of contiguously depositing on a substrate the first roughened layer having a deposited thickness of at least 1700 angstroms. A further metallic layer is then contiguously grown on the first roghened layer to form needles modeled as prolate spheroids having a length of at least 3500 angstroms and a width of at least 500 angstroms. In a specific embodiment, the needles are silver microneedles deposited from a vapor with a closed chamber and a vacuum pressure of at least $10^{-4}$ torr and at an evaporation rate from 2 to 20 angstroms per second. The silver microneedles are formed at a deposited thickness of at least 4000 angstroms as determined by a standard quartz thickness monitor.

67 Claims, 6 Drawing Sheets

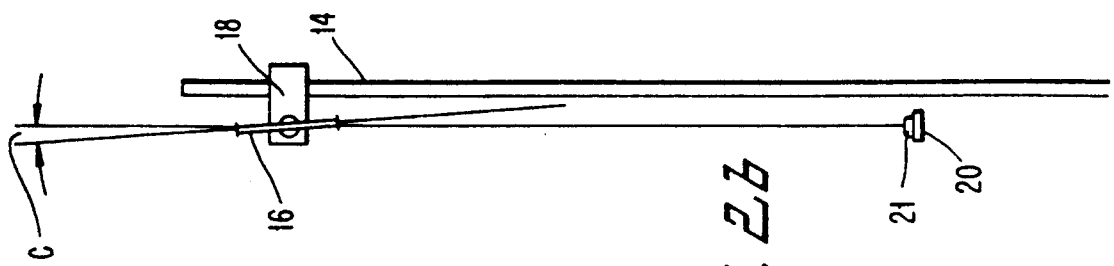
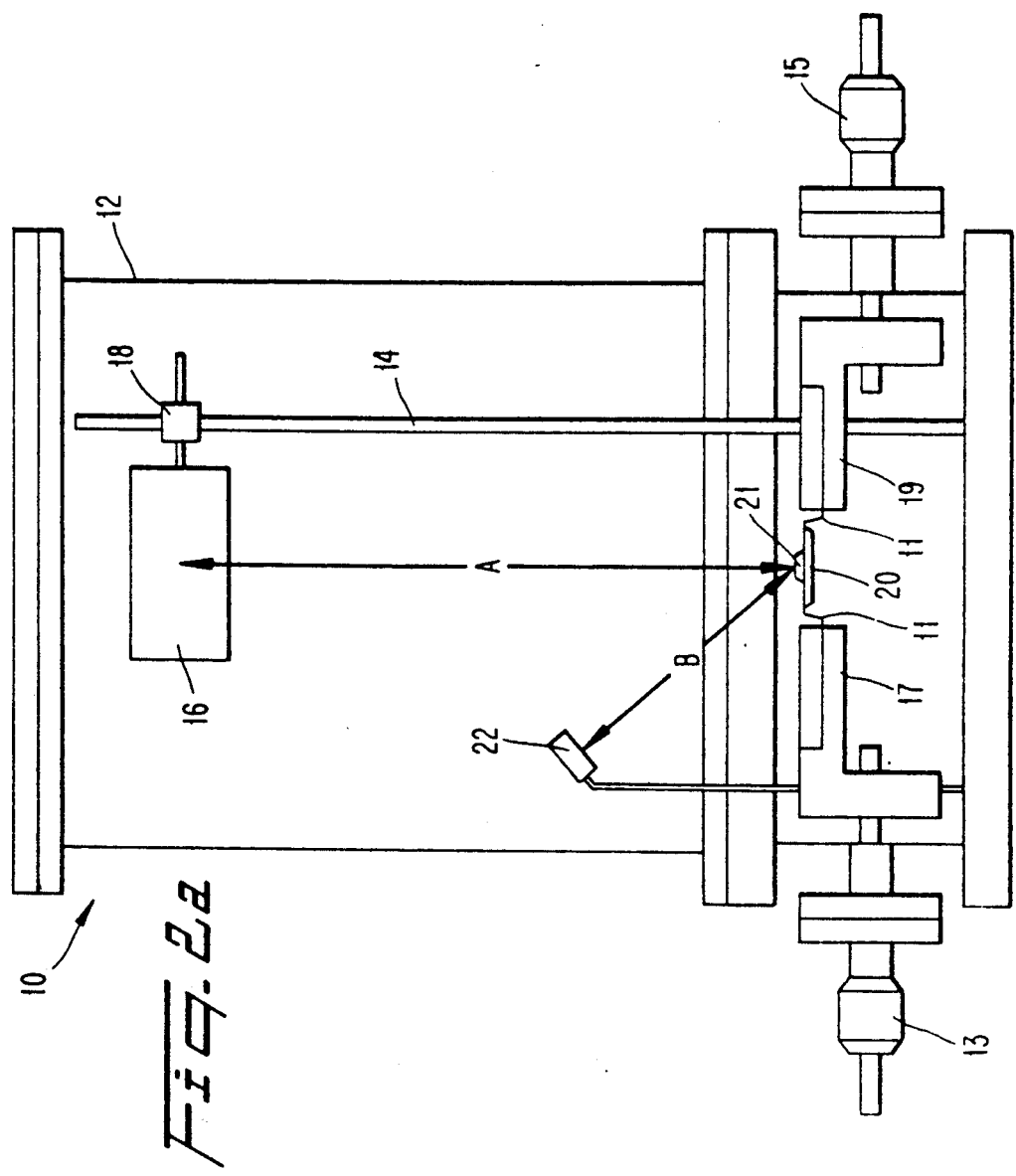

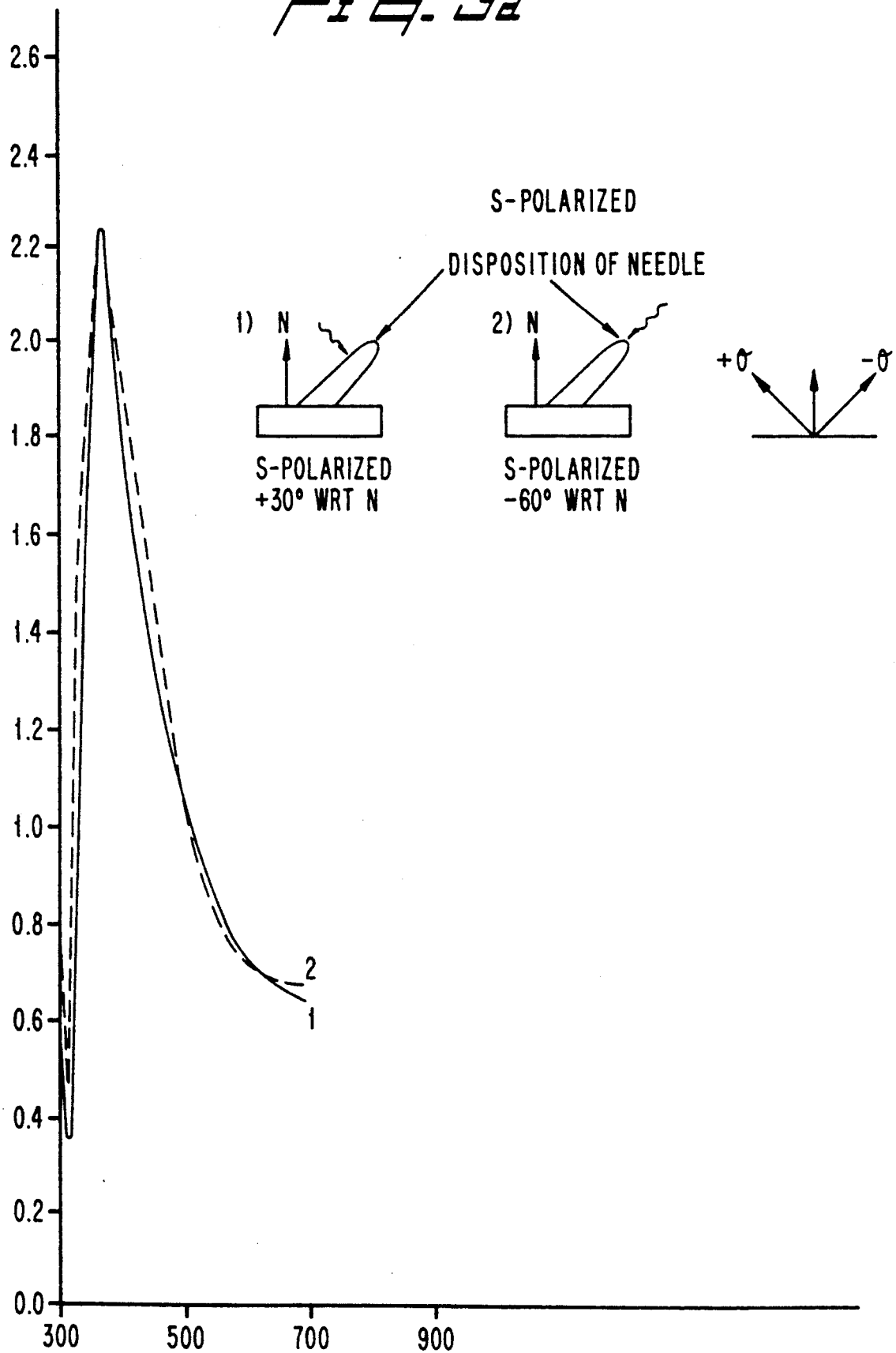

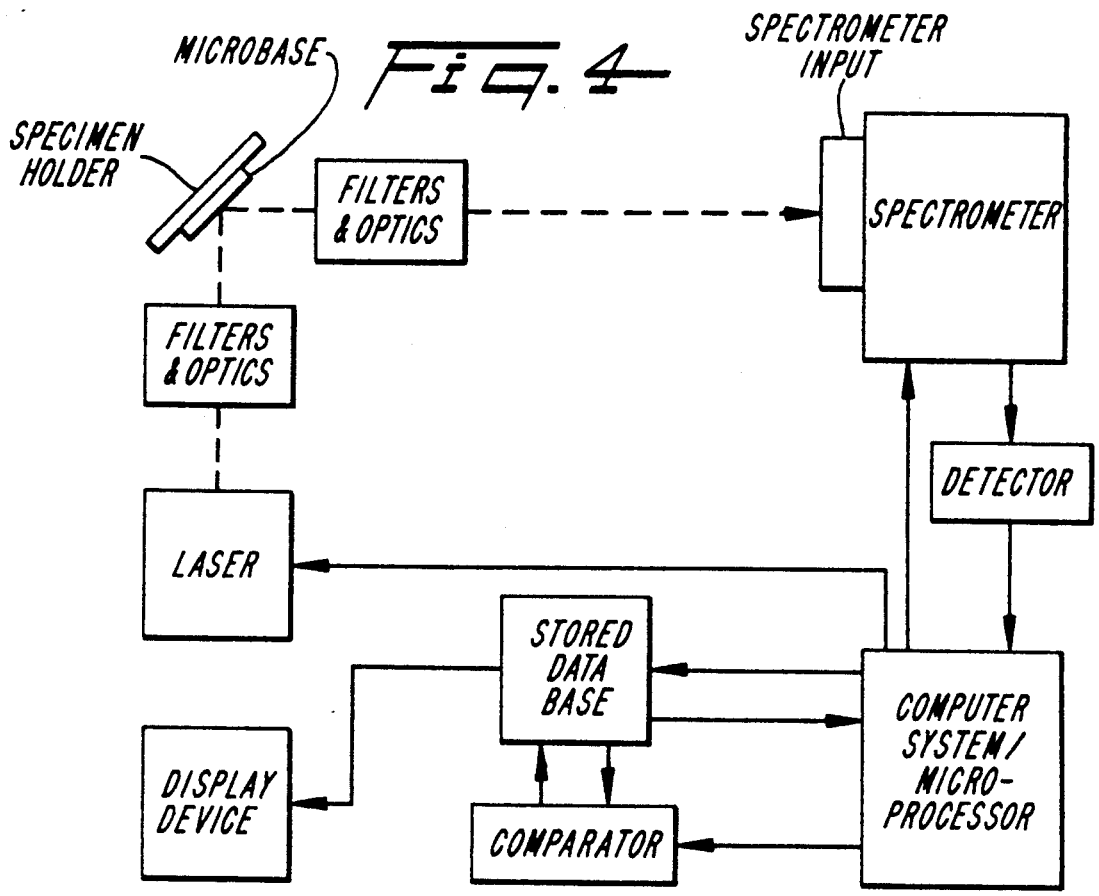
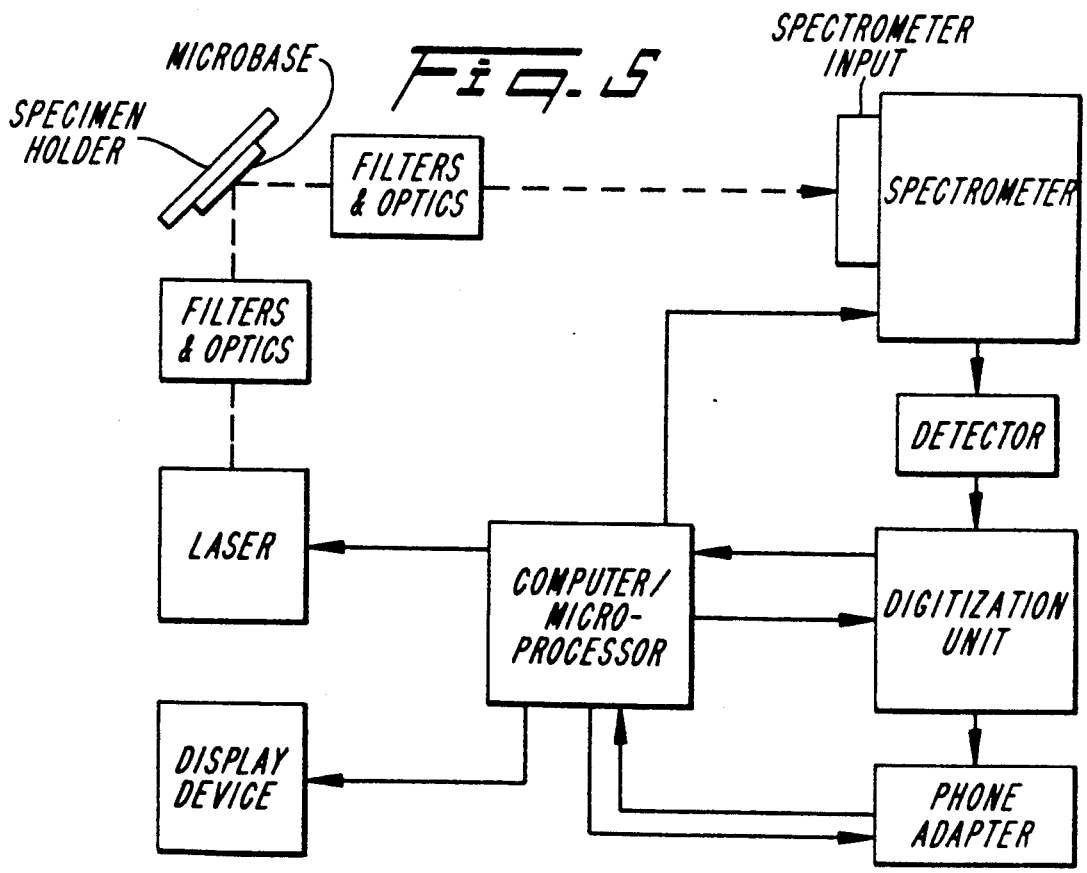

APPARATUS AND MICROBASE FOR SURFACE-ENHANCED RAMAN SPECTROSCOPY SYSTEM AND METHOD FOR PRODUCING SAME

FIELD OF THE INVENTION

This invention relates to the production and use of a microbase for a surface-enhanced Raman spectroscopy (SERS) system. More particularly, the invention relates to a microbase and an apparatus for using the microbase in the microanalytic examination of adsorbate specimens.

BACKGROUND OF THE INVENTION

Raman scattering was discovered by C. V. Raman in the 1920's when he observed that visible monochromatic light is colorshifted during light scattering by compounds dissolved in solution. Light incident on a molecule must be scattered from induced electronic dipoles for Raman scattering to occur.

A related phenomenon to Raman scattering is the absorptive scattering of infrared light from molecules. In this case, infrared light is absorbed as a molecule makes transition between various rotational or vibrational energy level. This results in reduced intensity at the energies corresponding to those transitions.

For Raman scattering, monochromatic light is scattered by an electronic transition which loses energy during the scattering, the energy being that of a transition from one rotational or vibrational level to another. The corresponding wavelength shifts in the light can be measured and provide a spectral signature for chemical identification similar to infrared light spectra. Such spectral signature is also known as a "fingerprint" or identification spectrum of the chemical material.

Knowledge of the relative intensities and positions of these scattered light signals are obtained from a monochromator that disperses visible light. An adequate spectrum of the target molecule can be obtained when a large enough portion of the spectrum is measured. Thus, the monochromator must be capable of analyzing light throughout the visible range and near the infrared region.

One of the major advantages of compound identification by Raman scattering is that even slightly different molecules will display unique Raman spectra. The accuracy of the Raman spectrum measurements is basically determined by the sensitivity of the light detector, the dispersion capability and other optical devices, and the ability of the compound to scatter Raman light.

If a compound is a good Raman scatterer, then the optics can be arranged to make high resolution measurements thereby increasing the ability to differentiate compounds. If the sample is not a good Raman scatterer, then appropriate alterations must be made in the experimental apparatus so that weak Raman light can be detected. Unfortunately, resolution is usually compromised when it is necessary to detect low light intensities and resolve the spectra of different compounds. Regardless, the Raman spectra will not change as long as the molecular structure is not altered or if nonlinear processes are not induced by large laser light intensities.

Various known reliably reproducible methods of material analysis include chromatography and mass spectrometry. However, these known techniques involve destruction of the specimen being analyzed. The primary advantages that Raman scattering detection processes have over conventional detection methods is that they are rapid and nondestructive, yield a "fingerprint" of the compound in question (i.e. the identification spectrum) with high sensitivity, and are applicable for measurements in or out of solution. As noted, gas chromatography, high performance liquid chromatography (HPLC) and mass spectrometry are destructive and relatively slow compared to Raman spectroscopy. Furthermore, infrared adsorption spectroscopy is not simple to perform in aqueous solutions since water strongly absorbs infrared light across a broad wavelength range.

The primary disadvantage of Raman scattering detection techniques is that Raman scattering is a weak process. Raman spectroscopy has low sensitivity requiring the use of powerful, costly laser sources for excitation. Lengthy experimental procedures and/or rather large quantities (milligrams) of the material being analyzed are sometimes required to obtain a good signal. The cost of the equipment is comparable to that of conventional detection methods.

The apparatus commonly used in Raman scattering includes a visible light laser, an optical spectrometer, and various optical devices such as lenses, light filters and mirrors. For Raman scattering measurements on bulk chemicals, the material is collected in some type of transparent container and laser light is allowed to strike the contents. Solid material may also be analyzed without containment in a sample vessel. The light scattered from the material is then collected by the lenses and other optical devices and focused into the entrance port of the spectrometer.

Measurement of the intensities and wavelengths of the scattered light is performed by the spectrometer. The empirical data is then transmitted to the data storage device which is usually a computer. The operator may then store the data or obtain a hard copy of the results obtained by the spectrometer.

Although this type of phenomenon has been known for years, to date, a good commercially useful Raman scattering spectroscopy system capable of achieving consistently reliable results still remains unavailable. In 1974, surface-enhanced Raman spectroscopy (SERS) was first discovered using an electrochemical cell having a solution with buffer agents. This particular type Raman spectroscopy system detects scattered monochromatic light from an adsorbate specimen constituting a target for a light beam. Compounds placed at the surface of a microbase may be analyzed and identified based upon their characteristic Raman spectrum. While compounds in solution will be adjacent the SERS-active surface, dry techniques have also been developed to coat the compounds being analyzed directly onto the SERS-active surface.

In 1978, the improvement referred to as surface-enhanced Raman spectrometry was explained as a particular form of the general field of surface analysis spectroscopy. The Raman scattering intensity for adsorbates on or near a special rough metal surface have been enhanced by factors of $10^3$ to $10^6$ times. Such known enhancements have been achieved at silver, copper and gold metal surfaces under both solution and dry vacuum conditions.

SERS studies have involved both the use of rigid and flexible substrates. Microscopically roughened surfaces have been covered with particles of metal such as silver or the like and used as supports for adsorbates in the SERS procedure. However, one of the recognized problems related to SERS is the lack of a practical substrate material that can be easily prepared and provide SERS data with sufficient reproducibility and accuracy for effecting commercial analytical purposes. U.S. Pat. No. 4,674,878 teaches the use of a flexible substrate and is incorporated in its entirety herein by reference.

Several known techniques are used for producing rigid microbase substrates. Such techniques include electrochemical roughening of electrode surfaces, a lithographic process and the prolate post or etched island method. Various types of microbodies including roughness-imparting microspheres, submicronsized beads and nonspherical particles such as submicron needles have been used to produce results with the SERS technique.

More specifically, substrates including SERS-active surfaces having microneedles with various shapes and sizes disposed thereon have been used for SERS analysis of materials. Although the possibility of developing a portable, SERS system has been contemplated, no known process presently exists to commercially produce microbases having consistently reliable SERS results to make such a portable SERS system feasible.

In a known method of producing a microbase, a 200 nm (nanometer) deposited film thickness of calcium fluoride provided a first roughened layer onto a glass substrate. Next, an 80 nm deposited thickness of silver metal was produced at normal incidence to form a good conducting layer. A final silver evaporation then took place at a grazing incidence and at a rate of 2 nm per second with the length of the submicron needles being almost equal to the total evaporation or deposited thickness. See article entitled "Optical Properties of Submicrometer-size Silver Needles" published May 15, 1988 in Volume 7, No. 14 of the Journal for the American Physical Society."

All deposited or evaporation film thicknesses are measured in a well known manner with a quartz crystal thickness monitor. All evaporations took place in a cryopumped electron beam evaporator at a vacuum pressure of $1 \times 10^{-6}$ torr. The average deposited thickness of the silver was reported at 210 nm and resulted in needles of approximately 200 nm or 2000 angstroms in length and 30 nm or 300 angstroms in width. Duplications of this reported experimental process failed to reproduce the results as reported in the May 15, 1988 article.

In another reported process for producing several microbases, a layer of calcium fluoride having a deposited thickness of 210 nm was first placed on a rigid substrate followed by the deposition of various evaporation or deposited thicknesses of 100, 150 and 200 nm of metals at deposition rates of 1 to 1.5 nm per second. The spaced distance between the evaporant crucible holding the metal being evaporated and the sample substrate on which the metal was being deposited was 30 cm. The sample was positioned at an incidence angle of 88° with respect to the evaporant crucible. A gold overlay of about 7 nm was disposed over the microneedles to prevent severe charging problems. See article in the Journal of the Optical Society of America, Volume 5, page 2552, December 1988 entitled "Surface Electromagnetic Modes in Prolate Spheroids of Gold, Aluminum, and Copper".

A further prior art technique is disclosed in a paper entitled "Optical and Microstructural Properties of Obliquely Evaporated Silver Films on Rough and Smooth Substrates." Various optical absorbance spectra are disclosed for obliquely evaporated silver films on microscope slides with either a 50 nm deposited layer of calcium fluoride or a 300 nm deposited layer of calcium fluoride. All evaporation or deposited thicknesses of the silver were monitored at 200 nm and the respective substrate slides placed at incidence angles of 89.3°, 89°, and 87.4°. No relationship is disclosed regarding the usefulness of these substrates in a SERS system. However, duplication of the reported process produced a target microbase which did not achieve commercially viable SERS data.

In another reported procedure, a 210 nm deposited layer of calcium fluoride was first placed on a microscope slide followed by a second contiguous 65 nm deposited layer of magnesium fluoride. Three silver evaporation or deposited thicknesses were tested on the two-layered surface at 100 nm, 200 nm, and 300 nm of evaporation as determined by the standard quartz monitor. All silver evaporations took place at an incidence angle of 88°.

Although the deposited or evaporation thickness as determined by the quartz thickness monitor reached 300 nm in these prior art processes, the length of the resultant needles attained a maximum of 200 nm or 2000 angstroms in length and 300 angstroms in width. Furthermore, attempts to consistently reproduce the reported microbase structures have been unsuccessful. In each of these prior art processes, the resultant microbases did not produce consistently reliable SERS results capable of achieving commercial reproducibility.

PURPOSE OF THE INVENTION

The primary object of this invention is to provide a process for preparing consistently operational microbases for producing reliable results in a SERS system.

A further object of the invention is to provide an efficiently operational SERS-active surface which can be consistently produced and provide effective reliably reproducible SERS analysis in microanalytical examinations.

Another object of the invention is to provide a SERS procedure capable of producing microanalytical examination of specimens heretofore unavailable for the numerous applications requiring accurate and reliable chemical analysis.

A still further object of this invention is to provide a target microbase adaptable for a portable SERS system for certain applications, and at the same time, useful for sophisticated operational SERS facilities maintaining a large computerized storage data base.

SUMMARY OF THE INVENTION

Several different features of the invention are disclosed herein. The primary discovery is directed to the structure of a target microbase useful to reliably obtain surface-enhanced Raman spectroscopy (SERS) data. The microbase comprises a substrate with a sample-adsorption surface including metal microneedles having a length sufficient to produce surface resonances that increase the intensity of the scattered Raman light signal for an adsorbate adjacent the sample-adsorption surface by a factor of at least $10^9$ times.

The specific embodiment of this microbase comprises a substrate having a first contiguous roughness layer composed of a dielectric material with a deposited thickness of at least 1700 angstroms and a second layer contiguously disposed on the first layer and including a plurality of metallic needles having a length of at least 3500 angstroms and a width of at least 500 angstroms. The needles are deposited on the second layer at a density in the range of from 70 to 80 needles per square micrometer. More particularly, the density is at least s70 needles per square micrometer.

In a specific embodiment, the sample-adsorption surface layer is effective to enhance a scattered Raman signal intensity for adsorbates adjacent the sample-adsorption surface by a factor of greater than $10^6$ times. A first contiguous roughness layer is placed on a substrate. The first roughness layer is composed of a dielectric material selected from the group consisting of calcium fluoride, magnesium fluoride or a metal oxide such as tin oxide and aluminum oxide. Any of the other well know dielectric materials useful in making this kind of layer for such a SERS microbase may be employed as long as it is within the established parameters of the present invention. The contiguously deposited dielectric material layer is sufficient to receive deposition of a metal such as silver which grows into a plurality of elongated microneedles having a length of at least 3500 angstroms and a width of at least 500 angstroms. The dielectric material layer has a deposited thickness of at least 1700 angstroms as determined by a quartz thickness monitor during the deposition process for the roughness layer.

When the metal is silver, it has been found necessary for the deposited thickness onto the first contiguous roughness layer to be at least 4000 angstroms to produce silver microneedles having a length of at least 4000 angstroms and a width of at least 500 angstroms. The aspect ratio for the metal microneedles of the invention are generally about 7 to 1 which ratio comprises the overall length of the needles compared to the overall width or diameter of the needles. The submicron needles have a prolate spheroidal shape when grown in accordance with the present invention. The density of the vapor deposited silver microneedles is in the range of from 70 to 80 needles per square micrometer. In a specific embodiment, the density of the deposited needles is 75 needles per square micrometer.

Another feature is directed to the process for producing the target microbase of the invention. The unexpected result is that every time the invention process is effected, a successful and usable microbase structure is produced. The substrate, whether flexible or rigid, is placed in an environment for vapor depositing a first contiguous roughened layer onto the surface of the substrate. Once the deposited thickness of the first layer is at least 1700 angstroms as determined by a thickness monitor device, the roughened layer is ready to receive the second contiguous metallic layer to be vapor deposited thereover.

The metallic needles are grown from a vapor produced via known techniques including either an electron beam assembly or a thermal boat apparatus. In either case, an evaporant container holds the metal to be evaporated a spaced distance from the microbase by an amount efficient to produce the prolate spheroidal needles. It has been unexpectedly found that, for the process of this invention, when the distance between the evaporant container and the microbase substrate is less than 31 centimeters, oblate spheroidal needles are formed. Such needles are flattened at the poles of the spheroidal structure and are unsatisfactory for obtaining consistently reliable SERS data. Thus, the distance between the evaporant container and the microbase substrate on which the metal is being vapor deposited must be at least 31 centimeters to produce the desired prolate spheroidal needle shape. The microbase substrate may provide any type of surface on which the roughened layer may be deposited. Such substrate may include mylar, a clean piece of cardboard, a rigid quartz microscope slide, a flexible tape and the like.

The heating of the evaporant container is controlled to produce an effective rate of evaporation of the metal for making the desired needles. It has been unexpectedly determined that the rate of evaporation from the evaporant container must be within the range from 2 to 20 angstroms per second as determined by known techniques in the field. Furthermore, the evaporation or incidence angle used to grow needles must be in the range of 86° to 88°. When growing silver microneedles, the incidence angle is at 87°. The metallic needles in accordance with this specific embodiment are grown by deposition from a vapor within a closed chamber at a vacuum pressure of at least $10^{-4}$ torr.

Another feature of the invention is directed to a surface-enhanced Raman spectroscopy apparatus comprising a radiant energy source for directing a beam of radiant energy toward the target microbase of the invention. The assembly includes means for exposing a predetermined portion of the sample-adsorption surface to the radiant energy source, means for positioning the predetermined portion of the sample-adsorption surface in a predetermined relationship with respect to the radiant energy source, and spectrometer means for detecting a scattered Raman signal from the predetermined portion of the sample-adsorption surface.

In a specific embodiment of the SERS apparatus, the radiant energy is a monochromatic light produced by a laser as the radiant energy source. The target microbase may be used in either an electrochemical cell or in accordance with a dry procedure wherein the adsorbate is dry and contiguously disposed on the sample-adsorption surface. To prepare the sample, a chemical to be analyzed is put into solution by dissolving it in a solvent such a cyclohexane, methanol or acetone. Once the chemical being analyzed is put into solution, an aliquot of the solution is placed onto the needles and allowed to dry. This leaves a minute residue of the dried adsorbate on the microbase which is then put into a SERS assembly.

Another feature of the invention is directed to a method of producing a surface-enhanced spectroscopy system for identifying adsorbate specimen materials. The method comprises providing a monochromatic light generator, a target microbase member and spectrometer means. The light generator is disposed to direct a beam of monochromatic light toward the target microbase member of the invention. The target microbase member is effective to support an amount of adsorbate sufficient to consistently enable reproducible identification of the adsorbate via the SERS operation.

A further feature of the invention is directed to an apparatus for performing a nondestructive analysis of a specimen material. The apparatus comprises a surface-enhanced Raman spectroscopy system including a radiant energy source, a target microbase having a SERS-active surface, means for exposing a predetermined portion of the SERS-active surface to the radiant energy source, means for positioning the predetermined portion of the SERS-active surface in a predetermined relationship with respect to the radiant energy source, and spectrometer means for detecting scattered Raman light signals from the predetermined portion of the SERS-active surface.

The SERS-active surface is disposed adjacent an amount of adsorbate sufficient to be analyzed by the SERS system. The spectrometer means includes input means and generating means for producing identification code signals representative of identification characteristics of the specimen material adsorbate being analyzed. The input means is adapted to receive specimen-related Raman scattering signals produced when the specimen material is exposed to radiant energy from the radiant energy source.

Focusing means direct the scattered Raman signals from the SERS-active surface to the input means of the spectrometer when the specimen material is exposed to the radiant energy. Generating means is adapted to produce identification code signals when the specimen-related scattering Raman signals are received by the input means. Comparator means matches the identification characteristics of the specimen material represented by the specimen-related identification code signals with identification characteristics of a plurality of known material standards stored in a data base to determine the identity of the specimen material or otherwise determine that a particular material is present. Display means are then used for indicating that the specimen material has been identified.

In a specific embodiment of this feature, the comparator means includes an automatically controlled storage data base including a plurality of material standards having known identification characteristics and specimen-related identification code response means adapted to access a computer storage data base to match the specimen-related identification characteristics with a known material standard. The generating means is portable and remotely located with respect to the comparative storage data base.

A further feature is a method of nondestructive microanalytical examination of materials using the apparatus of the invention. When the identification characteristics of known material standards are stored in a defined-storage data base, the process of the invention includes automatically program-controlling the generating of the identification code signals, the comparing of those code signals with identification characteristics of the known material standards to determine the identity of the specimen material, and the displaying of an indication that the adsorbate specimen material has been identified. The defined-storage data base may be located on a portable storage means such as a floppy or compact disc. The program-controlling step includes operatively connecting microprocessing means to the spectrometer means of the apparatus made in accordance of the invention.

BRIEF DESCRIPTION OF THE DRAWINGS

Other objects of this invention will appear in the following description and appended claims, reference being made to the accompanying drawings forming a part of the specification wherein like reference characters designate corresponding parts in the several views.

FIG. 2a is a front elevational view of an assembly for producing a microbase according to the invention;

FIG. 2b is a side elevational view of the assembly of FIG. 2a;

FIGS. 3a and 3b are graphical representations of absorbance characteristics of a target microbase with silver microneedles according to the invention;

FIG. 4 is a diagrammatic view of a program-controlled system according to the invention;

FIG. 5 is a diagrammatic view of another embodiment of a program-controlled system according to the invention.

DETAILED DESCRIPTION OF THE INVENTION

Figure 1:
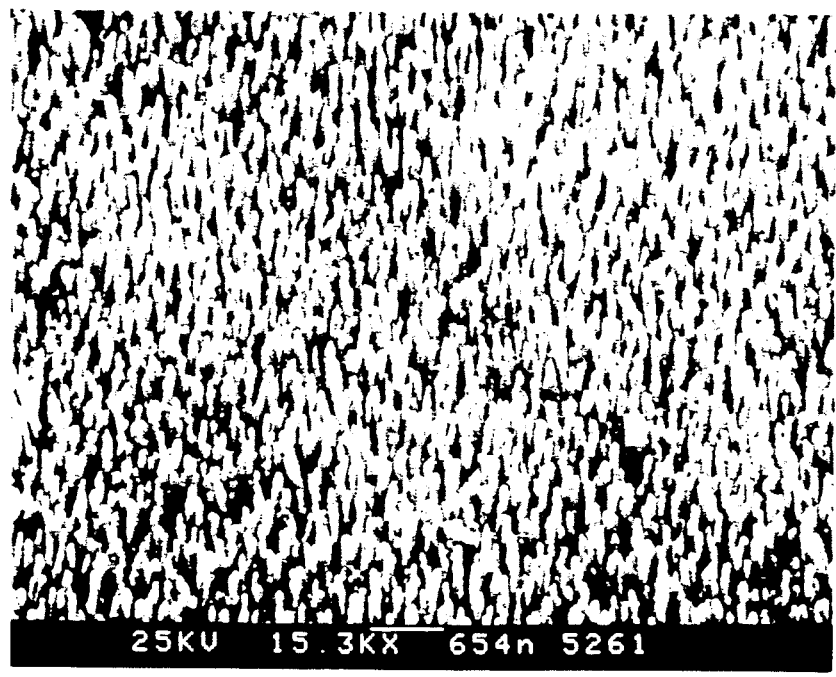
FIG. 1 is a photomicrograph of silver microneedles made in accordance with the invention.

In accordance with this invention, the photomicrograph of FIG. 1 shows a sample-adsorption surface of a target microbase including a plurality of submicron silver needles having a length of at least of 4,000 angstroms with a width of at least of 500 angstroms and a density of about 75 needles per square micrometer. The photomicrograph is at a multiplication of 15,300 times. Actual measurement of the needle length and width is made on photomicrographs at a multiplication exceeding 60,000 times.

FIGS. 2a and 2b show an assembly for the vacuum deposition or evaporation system for producing the microbase of the present invention. The vapor deposition assembly, generally designated 10, includes a vacuum housing 12 enclosing a vacuum chamber which operates at a vacuum pressure of at least $10^{-4}$. In specific embodiments, the vacuum pressure is reduced to as much as $10^{-6}$ and $10^{-7}$. The evaporator assembly 10 includes a tungsten thermal boat 20 mounted between electrical boat clamps 17 and 19 via boat connector tabs 11. The metal 21 disposed in tungsten boat 20 is evaporated when electrical power is fed through the high voltage feed mechanisms 13 and 15 to boat 20 via clamps 17 and 19 and connector tabs 11.

A slide stage 16 is mounted vertically above the tungsten boat 20 via a vertical rod 14 connected to slide stage 16 via coupling device 18. The relationship between metal 21 in boat 20 with respect to slide stage 16 is further shown in FIG. 2b with all of the other portions of the evaporator assembly 10 eliminated for purposes of clarity.

In this specific embodiment, slide stage 16 is disposed at an incidence angle C which is 3° from the vertical or 87° from a normal incidence angle. A microscope slide is fixedly placed on stage 16 and is at a spaced distance A directly above metal 21. It has been found that distance A between the microbase and evaporant boat 20 must be at least 31 centimeters to produce the desired prolate spheroidal shape to the microneedles of the invention. A crystal thickness monitor 22 is disposed at distance B (6 inches in this embodiment) from boat 20. This is a standard mechanism for measuring the rate of deposition of metal being evaporated from thermal boat 20. The same boat-to-stage relationship may be used when an electron beam is used to evaporate metal 21.

The assembly as shown in FIGS. 2a and 2b is for the metal deposition step. The first step of the procedure involves the placing of a clean, smooth, flat surface at a normal incidence angle with respect to the evaporant thermal boat. A dielectric material such as calcium fluoride is placed in thermal boat 20 and evaporated to be deposited onto the surface to produce the desired first roughness layer. Normal incidence is defined as when a vector is perpendicular to the flat surface and passes through the source. That is, stage 16 is 90° or normal to the vertical line extending upwardly from boat 20. Once the roughness layer is formed, it is then a matter of evaporating metal 21 such as silver which moves upwardly to the microbase surface at an incidence angle of 87°. Thermal boat 20 is heated at an amount sufficient to produce a rate of evaporation of metal 21 to be in the range of 2 to 20 angstroms per second. If the rate of evaporation is greater than this, the desired shape of the needles is not obtained.

Figure 3B:
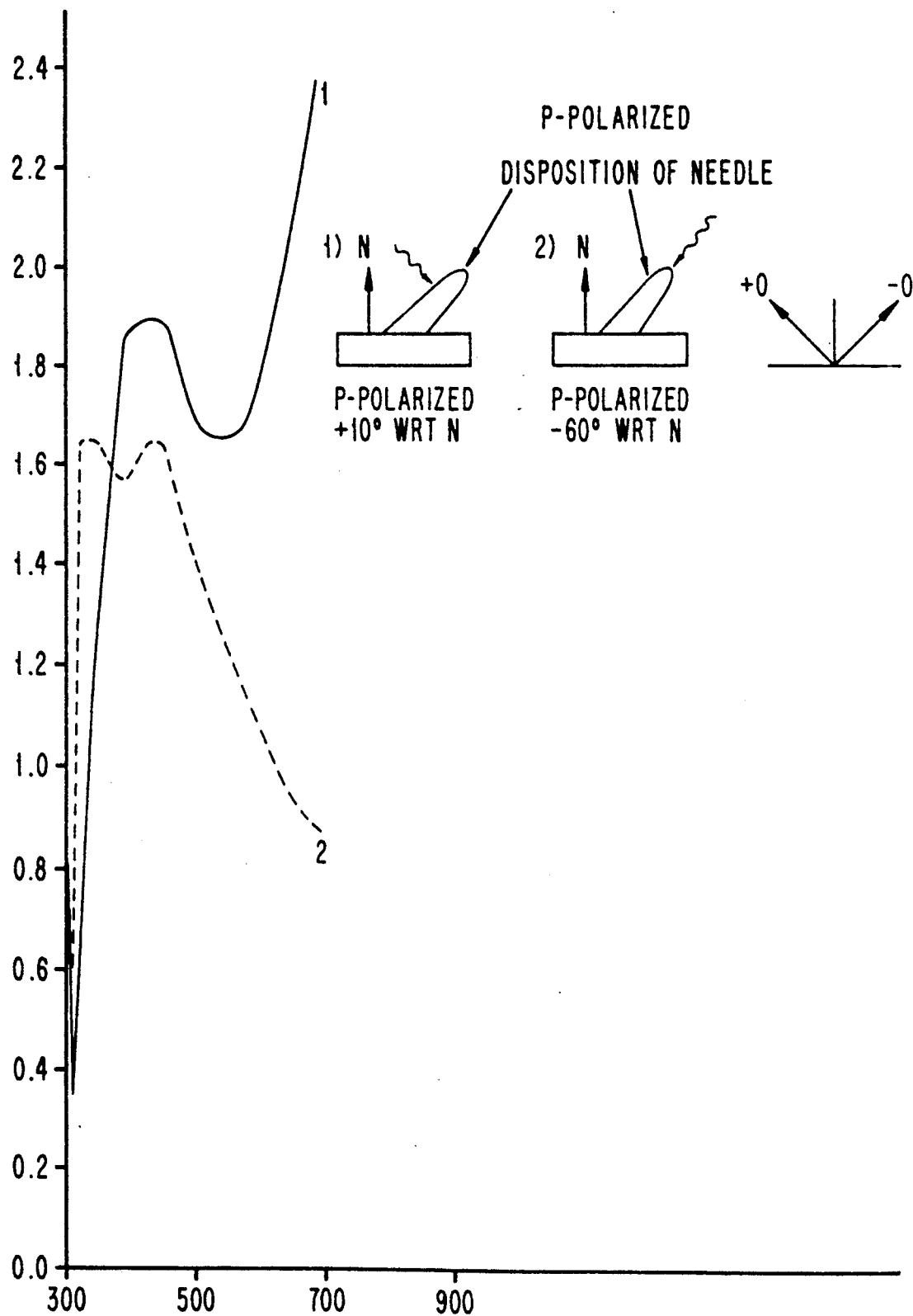

Optical characteristics for silver microneedles according to the invention is shown in FIGS. 3a and 3b. Where the prior art has attained to an absorbance of about 0.45 for silver and up to about 1.0 for gold, the microbase surface in a specific embodiment of this invention has an attained absorbance of greater than 2.4. As is well known, these absorbance numbers indicate to what extent the metal needles will absorb light.

When the laser light wavelength is at about 700 nm, prior art silver needles attained an absorbance of a little over 0.7. With a specific embodiment of the silver microbase of the present invention with p-polarized at +10° with respect to the normal as shown in FIG. 3b, the absorbance is shown to be increasing at 2.4. It is contemplated that wavelengths longer than 700 nm will produce even greater absorbance. The absorbance peaked at about 2.25 with s-polarized light at both +30° and −60° with respect to the normal.

A specific embodiment of a SERS assembly is shown in FIG. 4 and is designed to address a more sophisticated type of system. The laser, microbase and spectrometer assembly is fundamentally the same as in all SERS applications. The photon detector receives the information related to the adsorbate material being analyzed and directs it to the computer system or microprocessor. The microbase holder may be designed to hold either a single microbase or designed for an automated system having the capability of holding a plurality of microbases so that sequential readings could be made on a plurality of adsorbate specimens.

Figure 6:
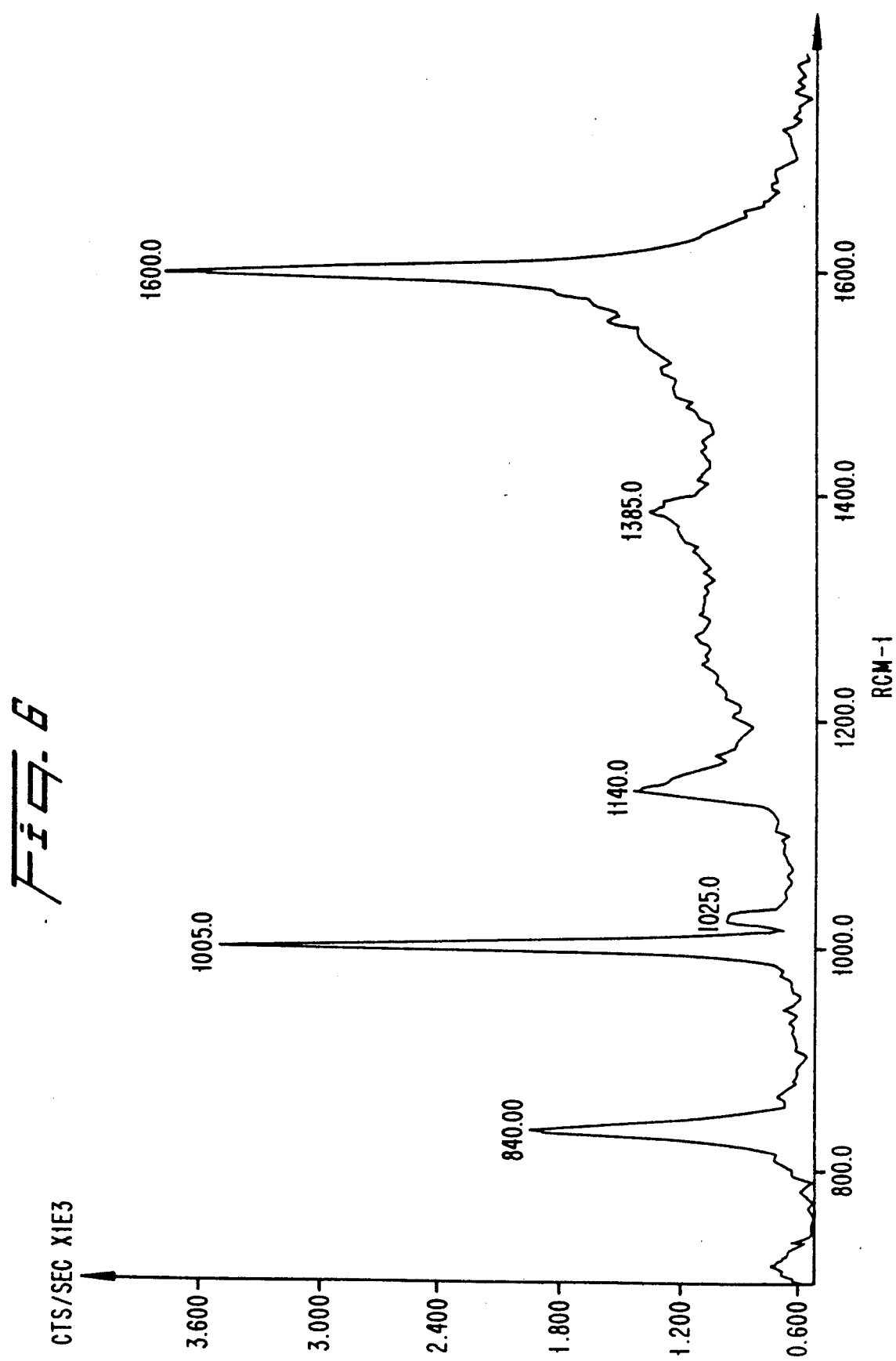
FIG. 6 is a graphical representation of a SERS identification spectrum for benzoic acid.

The computer receives the identification code signals from the detector of the spectrometer means and then sends a signal to a stored data base and comparator for the purpose of matching the unknown identification characteristics to a plurality of identification characteristics associated with a number of standards. An example of such a standard is shown in FIG. 6. Such SERS spectra standards are readily available for numerous materials useable for this type operation. Once the identification code signals of the adsorbate specimen are matched to the appropriate standard, a display device is used to either display the actual identification of the material or simply to indicate whether a particular type of material is present in the adsorbate specimen.

The embodiment of a program-controlled system useful for a portable application is shown in FIG. 5. Here a digitization unit is used to digitize the identification code signal coming from the detector of the spectrometer means. The device would have no automated microbase holder such as in the more sophisticated permanent defined-storage unit. However, it is possible that a floppy or compact disk could be used for storing the plurality of identification characteristics of numerous standards for insertion into a computer assembly. This particular illustrated system includes a phone adaptor to which the information is initially fed to a base terminal at a central location. The matching of the identification code signals may take place at the central location or on site via either a floppy disk or compact disk in this particular embodiment. The indication of the presence of a particular material or its actual identity is then sent back to the field site for the person to then take further appropriate action.

The system of FIG. 5 is designed for portability and ruggedness. Connectors for this unit may be fiber optics where the microbase unit would be a probe with the needles deposited on a fiber optic or probe unit which could then be used for analyzing liquids, gases or solids depending upon the particular environment and the material being analyzed.

The units of the present invention are useful for numerous applications including (1) the detection of contamination of pesticides and other hazardous materials in agricultural products and in food and water supplies; (2) the detection and identification of controlled substances in connection with law enforcement activities; (3) the detection of substances and solutions by hospital and commercial laboratories; (4) effecting quality control in the chemical and petrochemical industries; and (5) study and research by educational institutions.

Specifically, the assemblies of the invention are useful for determining the type and concentration of materials at municipal incinerators, landfill sites and solid waste processing sites; at import facilities for food and fiber basic materials; at manufacturing sites for guaranteeing the purity of product being produced; at inspection sites for testing trucks, trains or other vehicles involved in transporting toxic substances; hazardous waste sites: and electric energy generation sites for monitoring the air, water and waste streams for safety compliance requirements. The system of this invention is far superior in speed, cost and accuracy with respect to the current state of the art in testing methods. Current devices are relatively slow and destructive as noted above.

It has been found that the optical data for the microbase of the present invention will unexpectedly produce more than two times better absorbance characteristics with the same aspect ratios for the microneedles being formed. It has been determined further that upon increasing the intensity of the scattered Raman light, it is possible to use either lower laser power or detect a smaller amount of the specimen compound using the same laser power.

For a given molecular concentration on the sample-adsorption surface for a given laser power, the microbase of the present invention will give a better scattered Raman light signal and be much more consistent in its intensity and result than known prior art microbases. Thus, with the microbase of the present invention it is possible to obtain consistent and reliably reproducible SERS results using a detector that is less expensive and does not have to be as sensitive as with known prior art microbases at a lower laser power. By reducing the required amount of radiant source light or the amount of compound to analyze the specimen for the same amount of sensitivity for a detector, then the feasibility of a commercially acceptable SERS system is significantly increased.

It has been unexpectedly found that with silver needles, the length must be at least 4000 angstroms with the width at least 500 angstroms to achieve the desired SERS results. However, with different metals and different laser lines, the length, width and density of the microneedles must be effective to produce a SERS intensity sufficient to obtain reliable and repeatable data in the spectrometer analysis. To date, no prior art microbase having submicrometer length needles can produce a reliably reproducible Raman intensity to consistently perform a SERS procedure for commercial purposes.

The overall absorbance of the microbase is what determines the reflectivity of the silver microneedles which, in turn, is what determines the intensity of the scattered Raman light useful in conducting the SERS procedure. It has been discovered that if the size and shape of these silver needles can be maintained while increasing the amount of silver in accordance with the invention, an appropriate reproducible SERS procedure can be effected.

In a SERS procedure, the light from the laser is converted from electromagnetic energy to a surface plasmon which is a surface oscillation of the conducting electrons in the sample-adsorption metallic surface. The light of the SERS procedure is polarizing the electrons on the sample-adsorption surface. This is where the intense electric field comes from which actually significantly increases the probability that a molecule will scatter Raman light. The more light that can be absorbed by the surface particles, the greater is the probability of the Raman scattering.

It is well known that no direct correlation exists between the generation of the surface plasmon with respect to the intensity of the absorbance data or the intensity of the scattered Raman light. Consequently, it is deemed totally unexpected that the production of silver microneedles having a length of at least 4000 angstroms and a width of at least 500 angstroms and at a density of about 75 needles per square micrometer achieves the experienced reproducible SERS results. For the first time, the microbase of the present invention is able to produce the kind of surface plasmon characteristics which will enable the conducting of a consistent and reliable SERS procedure.

A particular wavelength of laser light will excite the surface plasmon to produce a scattered Raman light for identifying the type and concentration of materials in the specimen being analyzed. With the microbase production method of the present invention, it is now possible to adjust the length of the microneedles being formed to move the desired resonance up or down onto the particular laser line that is available for use. For example, there may be a large number of materials such as pesticides for which surface plasmon excitation will take place at a laser light wavelength of 710 nm. However, if no laser is available to produce that size wavelength, the results can be directly effected by adjusting the length of the metallic needle being grown on the microbase roughness layer.

In other words, as the length, width and density of the metallic needle is changed, the particular wavelength of laser light that will excite surface plasmon will be changed. The resonances of the plasmon are determined by the length, width, density and aspect ratios of the microneedles and the dielectric function of the roughness layer material. If it is decided to have a particle with a surface plasmon that can be excited by a 750 nm laser light, by using the vapor deposition techniques of the present invention, the microneedle can be made with the appropriate characteristics to achieve the desired surface plasmon resonance for producing the necessary intensity of scattered Raman light.

Quite unexpectedly, the present invention now makes it possible to fine tune the structure of the microbase for consistently performing reliable and reproducible SERS data. The present invention has developed a manufacturing process technique based upon the optical characteristics of the target microbase itself with the processing steps for fabricating the microbase being directly correlated for the first time with the consistent production of reliable SERS data.

While the apparatus and microbase for surface-enhanced Raman spectroscopy system and method for producing same has been shown and described in detail, it is obvious that this invention is not to be considered as limited to the exact form disclosed, and that changes in detail and construction may be made therein within the scope of the invention without departing from the spirit thereof.

What is claimed is:

1. A surface-enhanced Raman spectroscopy assembly comprising:
   (a) a radiant energy source for directing a beam of radiant energy toward a target microbase,
   (b) said target microbase including a substrate, a first roughened surface layer contiguously disposed on the substrate, and a sample-adsorption surface layer contiguously disposed on said first roughened layer, and
   (c) said sample-adsorption surface layer being effective to enhance a scattered Raman signal intensity for adsorbates adjacent said sample-adsorption surface layer by a factor of greater than $10^6$ times,
   (d) said sample-adsorption surface including a plurality of submicron needles having a length of at least 3500 angstroms and a width of at least 500 angstroms,
   (e) means for exposing a predetermined portion of the sample-adsorption surface to said radiant energy source,
   (f) means for positioning said predetermined portion of the sample-adsorption surface in a predetermined relationship with respect to said radiant energy source, and
   (g) spectrometer means for detecting a surface Raman signal from said predetermined portion of said sample adsorption surface.

2. An assembly as defined in claim 1 wherein an adsorbate is dry and contiguously disposed on the sample-adsorption surface.

3. An assembly as defined in claim 1 wherein the needles have a density of at least 70 needles per square micrometer.

4. An assembly as defined in claim 1 wherein said first roughened layer has a deposited thickness of at least 1700 angstroms.

5. An assembly as defined in claim 4 wherein the first roughened layer is composed of a dielectric material.

6. An assembly as defined in claim 5 wherein the dielectric material is an oxide material.

7. An assembly as defined in claim 5 wherein the dielectric material is selected from the group consisting of calcium fluoride, magnesium fluoride, tin oxide and aluminum oxide.

8. An assembly as defined in claim 5 wherein the dielectric material is calcium fluoride.

9. An assembly as defined in claim 1 wherein the target microbase is the product of a process comprising the steps of:
   (a) contiguously depositing on a substrate the first roughened layer having a deposited thickness of at least 1700 angstroms, and then (b) contiguously growing on the first roughened layer metallic needles modelled as prolate spheroids having a length of at least 3500 angstroms and a width of at least 500 angstroms.

10. An assembly as defined in claim 9 wherein the first roughened layer is composed of calcium fluoride.

11. An assembly as defined in claim 10 wherein the metallic needles are grown by deposition from a metallic vapor within a closed chamber at a vacuum pressure of at least $10^{-4}$ torr.

12. An assembly as defined in claim wherein the metallic vapor is produced by heating an evaporant container to evaporate metal therefrom at a rate from 2 to 20 angstroms per second.

13. An assembly as defined in claim 11 wherein an evaporant container holding the metal to be evaporated is spaced a distance from the microbase by an amount sufficient to produce said metallic needles as prolate spheroids.

14. An assembly as defined in claim 13 wherein the distance between the evaporant container and said microbase is at least 31 centimeters.

15. An assembly as defined in claim 14 wherein the evaporant container is a thermal boat.

16. An assembly as defined in claim 9 wherein the substrate with the first roughened layer thereon is positioned on an incidence angle of from 86° to 88° with respect to an evaporant container which is located a spaced distance below said microbase.

17. An assembly as defined in claim 16 wherein the incidence angle is 87°.

18. An assembly as defined in claim 9 wherein the metallic needles are grown by deposition from a metal vapor within a closed chamber at a vacuum pressure of at least $10^{-6}$ torr.
said metal deposited from the metal vapor has a deposited thickness of at least 4000 angstroms as determined by a standard quartz thickness monitor.

19. An assembly as defined in claim 18 wherein the metal deposited from the metal vapor is silver.

20. An assembly as defined in claim 19 wherein the length of the silver needles is at least 4000 angstroms.

21. An assembly as defined in claim 20 wherein the first roughened layer is composed of calcium fluoride.

22. An assembly as defined in claim 1 wherein said radiant energy source produces a collimated monochromatic light.

23. An assembly as defined in claim 1 wherein said radiant energy source is a laser.

24. A method of producing a surface-enhanced Raman spectroscopy system (SERS) for identifying specimen materials, said method comprising:
  (a) providing a monochromatic light generator, a target microbase member and spectrometer means,
  (b) disposing the light generator to direct a beam of monochromatic light toward the target microbase member having a sample-adsorption surface layer, and
  (c) positioning the target microbase member with respect to the light generator as a light source to receive said beam and direct scattered Raman signals toward the spectrometer means for measuring selected characteristics of the Raman signals wherein the intensity for adsorbates adjacent said sample-adsorption layer is enhanced at the sample-adsorption surface layer by a factor of greater than $10^6$ times,
  (d) said providing step including preparing the target microbase member to support an amount of adsorbate sufficient to consistently enable reproducible identification of the adsorbate via the SERS operation.

25. A method of producing a microbase for use in a surface-enhanced Raman spectroscopy system for identifying adsorbates, said method comprising:
  (a) providing a substrate having a contiguous roughness layer sufficient to receive deposition of a metal which grows into a plurality of elongated microneedles having a length of at least 500 angstroms and a width of at least 500 angstroms,
  (b) placing said substrate into an enclosed vacuum chamber a spaced distance from an evaporant container holding a supply of metal to be contiguously deposited onto said roughness layer,
  (c) locating the substrate roughness layer at an incidence angle of 87 degrees with respect to the evaporant container, and
  (d) evaporating the metal from said evaporant container at a rate from 2 to 20 angstroms per second,
  (e) said spaced distance between the substrate and evaporant container being sufficient to produce prolate spheroidal needles at a density from 70 to 80 needles per square micrometer.

26. A method as defined in claim 25 wherein said spaced distance between the substrate and the evaporant container is greater than 31 centimeters.

27. A method as defined in claim 25 wherein said roughness layer has a deposited thickness of at least 1700 angstroms.

28. A method as defined in claim 27 wherein the roughness layer is composed of a dielectric material.

29. A method as defined in claim 28 wherein the dielectric material is calcium fluoride.

30. A method as defined in claim 25 wherein the needles are grown by deposition from a metal vapor within a closed chamber at a vacuum pressure of at least $10^{-4}$ torr,
said metal deposited from the metal vapor has a deposited thickness of at least 4000 angstroms as determined by a standard quartz thickness monitor.

31. A method as defined in claim 30 wherein the needles are silver and have a length of at least 4000 angstroms.

32. A method as defined in claim 31 wherein the roughness layer has a deposited thickness of at least 1700 angstroms.

33. A method as defined in claim 32 wherein the roughness layer is composed of calcium fluoride.

34. A portable, surface-enhanced Raman spectroscopy system (SERS) comprising:
  (a) a microbase including a sample-adsorption surface effective to enhance a Raman scattered light signal, and
  (b) a light source for producing a scattered Raman light signal from the microbase,
  (c) said sample-adsorption surface including metallic microneedles having a prolate spheroidal shape sufficient to produce surface resonances that increase the intensity of the scattered Raman light signal for an adsorbate adjacent the sample-adsorption surface by a factor of greater than $10^9$ times, (d) said microneedles have a length, width and density in amounts effective to produce surface plasmon characteristics at the sample-adsorption surface for receiving consistently reliable SERS procedure results.

35. A system as defined in claim 34 wherein
said sample-adsorption surface includes elongated metallic microneedles having a length of at least 3500 angstroms and a width of at least 500 angstroms.

36. A system as defined in claim 35 wherein
the density of the microneedles is in the range of from 70 to 80 needles per square micrometer.

37. A target microbase for use in surface-enhanced Raman spectroscopy, said microbase comprising:
(a) substrate having a first contiguous roughness layer composed of a dielectric material with a thickness of at least 700 angstroms, and a second layer contiguously disposed on said first layer and including a plurality of metallic needles having a length of at least 3500 angstroms and a width of at least 500 angstroms,
(b) said needles being deposited on said second layer at a density of at least 70 needles per square micrometer.

38. A target microbase as defined in claim 37 wherein
the dielectric material is calcium fluoride and the metallic needles are composed of silver having a length of at least 4000 angstroms and a density of 75 needles per square micrometer.

39. An apparatus for producing a nondestructive analysis of a specimen material, said apparatus comprising:
(a) a surface-enhanced Raman spectroscopy (SERS) system including a radiant energy source, a target microbase having a SERS-active surface, means for exposing a predetermined portion of the SERS-active surface to said radiant energy source, means for positioning said predetermined portion of the SERS-active surface in a predetermined relationship with respect to the radiant energy source, and spectrometer means for detecting surface scattering Raman signals from said predetermined portion of the SERS-active surface;
(b) said SERS-active surface including a first roughened layer contiguously disposed on a substrate, and a sample-adsorption surface contiguously disposed on the first roughened layer and including elongated metallic microneedles having a length of at least 3500 angstroms and width of at least 500 angstroms, said SERS-active surface being disposed adjacent an amount of adsorbent specimen material sufficient to be analyzed by said SERS system;
(c) said spectrometer means including input means and generating means for producing identification code signals representative of identification characteristics of the specimen material being analyzed;
(d) said input means being adapted to receive specimen-related scattered Raman signals produced when the specimen material is exposed to radiant energy from the radiant energy source;
(e) means for directing, to said input means, specimen-related surface-enhanced scattered Raman signals produced when the specimen material at the SERS-active surface is exposed to said radiant energy;
(f) said generating means being adapted to produce said identification code signals when the specimen-related scattered Raman signals are received by the input means;
(g) comparator means for matching the identification characteristics of the specimen material represented by the specimen-related identification code signals with identification characteristics of known material standards to determine the identity of the specimen material; and
(h) display means for indicating that the specimen material has been identified.

40. An apparatus as defined in claim 39 wherein
said specimen material is dry and contiguously disposed on the SERS-active surface.

41. An apparatus as defined in claim 39 wherein the microneedles have a density in the range of 70 to 80 needles per square micrometer.

42. An apparatus as defined in claim 39 wherein
the comparator means includes a computer storage data base including a plurality of material standards having known identification characteristics and specimen-related identification code response means adapted to access the storage data base to match the specimen-related identification characteristics with the known material standard identification characteristics.

43. An apparatus as defined in claim 42 wherein
said generating means is portable and remotely located with respect to said computer storage data base.

44. An apparatus for producing a nondestructive analysis of a specimen material, said apparatus comprising:
a surface-enhanced Raman spectroscopy (SERS) system including a radiant energy source, a target microbase having a SERS-active surface, means for exposing a predetermined portion of the SERS-active surface to said radiant energy source, means for positioning said predetermined portion of the SERS-active surface in a predetermined relationship with respect to the radiant energy source, and spectrometer means for detecting surface scattering Raman signals from said predetermined portion of the SERS-active surface;
(b) said SERS-active surface being disposed adjacent an amount of adsorbent specimen material sufficient to be analyzed by said SERS system;
(c) said spectrometer means including input means and generating means for producing identification code signals representative of identification characteristics of the specimen material being analyzed;
(d) said input means being adapted to receive specimen-related scattered Raman signals produced when the speciment material is exposed to radiant energy from the radiant energy source;
(e) means for directing to said input means, specimen-related surface-enhanced scattered Raman signals produced when the specimen material at the SERS-active surface is exposed to said radiant energy;
(f) said generating means being adapted to produce said identification code signals when the specimen-related scattered Raman signals are received by the input means;
(g) comparator means for matching the identification characteristics of the specimen material represented by the specimen-related identification code signals with identification characteristics of known material standards to determine the identity of the specimen materials; and (h) display means for indicating that the specimen material has been identified;

(i) said target microbase including a first roughened layer contiguously disposed on a substrate and a sample-adsorption surface contiguously disposed on first roughened layer;

(j) said first roughened layer has a deposited thickness of at least 1700 angstroms.

45. An apparatus as defined in claim 44 wherein the first roughened layer is composed of a dielectric material.

46. An apparatus as defined in claim 45 wherein the dielectric material is an oxide material.

47. An apparatus as defined in claim 45 wherein the dielectric material is selected from the group consisting of calcium fluoride, magnesium fluoride, tin oxide and aluminum oxide.

48. An apparatus as defined in claim 45 wherein the dielectric material is calcium fluoride.

49. An apparatus for producing a nondestructive analysis of a specimen material, said apparatus comprising:

(a) a surface-enhanced Raman spectroscopy (SERS) system including a radiant energy source, a target microbase having a SERS-active surface, means for exposing a predetermined portion of the SERS-active surface to said radiant energy source, means for positioning said predetermined portion of the SERS-active surface in a predetermined relationship with respect to the radiant energy source, and spectrometer means for detecting surface scattering Raman signals from said predetermined portion of the SERS-active surface;

(b) said SERS-active surface being disposed adjacent an amount of adsorbent specimen material sufficient to be analyzed by said SERS system;

(c) said spectrometer means including input means and generating means for producing identification code signals representative of identification characteristics of the specimen material being analyzed;

(d) said input means being adapted to receive specimen-related scattered Raman signals produced when the specimen material is exposed to radiant energy from the radiant energy source;

(e) means for directing, to said input means, specimen-related surface-enhanced scattered Raman signals produced when the specimen material at the SERS-active surface is exposed to said radiant energy;

(f) said generating means being adapted to produce said identification code signals when the specimen-related scattered Raman signals are received by the input means;

(g) comparator means for matching the identification characteristics of the specimen material represented by the specimen-related identification code signals with identification characteristics of known material standards to determine the identity of the specimen material;

(h) display means for indicating that the specimen material has been identified; and (i) the target microbase is the product of a process comprising the steps of: (1) contiguously depositing on a substrate a roughened layer having a deposited thickness of at least 1700 angstroms, and then (2) contiguously growing on the roughened layer metallic needles modeled as prolate spheroids having a length of at least 3500 angstroms and a width of at least 500 angstroms.

50. An apparatus as defined in claim 49 wherein the roughened layer is composed of calcium fluoride.

51. An apparatus as defined in claim 50 wherein the metallic needles are grown by deposition from a metallic vapor with a closed chamber at a vacuum pressure of at least $10^{-4}$ torr.

52. An apparatus as defined in claim 51 wherein the metallic vapor is produced by heating an evaporant container to evaporate metal therefrom at a rate from 2 to 20 angstroms per second.

53. An apparatus as defined in claim 52 wherein an evaporant container holding the metal to be evaporated is spaced a distance from the substrate by an amount sufficient to produce prolate spheroidal needles 54. An apparatus as defined in claim 53 wherein the distance between the evaporant container and said substrate is at least 31 centimeters.

55. An apparatus as defined in claim 53 wherein the evaporant container is a thermal boat.

56. An apparatus as defined in claim 49 wherein the substrate with the roughened layer thereon is positioned on an incidence angle of from 86° to 88° degrees with respect to an evaporant container located a spaced distance below said substrate.

57. An apparatus as defined in claim 56 wherein the incidence angle is 87°.

58. An apparatus as defined in claim 49 wherein the metallic needles are grown by deposition of a metal from a vapor within a closed chamber at a vacuum pressure of at least $10^{-4}$ torr,
said metal has a deposited thickness of at least 4000 angstroms as determined by a standard thickness monitor.

59. An apparatus as defined in claim 58 wherein the metal is silver and the length of the needles is at least 4000 angstroms.

60. An apparatus as defined in claim 59 wherein the needles have a density of at least 75 microneedles per square micrometer.

61. An apparatus as defined in claim 60 wherein the roughened layer is composed of calcium fluoride.

62. A method of nondestructive microanalytical analysis of materials, said method comprising:

(a) providing surface-enhanced Raman spectroscopy (SERS) system including a radiant energy source, means for exposing a predetermined portion of a SERS-active surface to said radiant energy source, means for positioning said predetermined portion of the SERS-active surface in a predetermined relationship with respect to the radiant energy source, and spectrometer means for detecting surface scattered Raman signals from said predetermined portion of the SERS-active surface;

(b) providing a target microbase having a SERS-active surface including a first roughened layer contiguously disposed on a substrate, and a sample-adsorption surface contiguously disposed on the first roughened layer, said sample-adsorption surface including metallic microneedles having a length of at least 3500 angstroms and a width of at least 500 angstroms, and placing the SERS-active surface adjacent an amount of adsorbent specimen material sufficient to be analyzed;

(c) said spectrometer means including means for generating identification code signals representative of identification characteristics of the adsorbent material being analyzed at the SERS-active surface;

(d) providing the identification characteristics of a plurality of known material standards with which the identification code signals of the specimen material may be compared;

(e) said spectrometer means including input means for receiving scattered Raman signals produced when the specimen material is exposed to radiant energy from the radiant energy source;

(f) exposing the adsorbent specimen material to radiant energy from the radiant energy source to produce specimen-related surface-enhanced scattered Raman scattering signals;

(g) directing said specimen-related surface-enhanced scattered Raman signals to said input means of the spectrometer means;

(h) generating specimen-related identification code signals in response to said specimen-related scattered Raman signals;

(i) comparing the specimen-related identification code signals with the identification characteristics of the known material standards to determine the identity of the specimen material; and (j) displaying an indication that a particular type of material is present in the specimen material.

63. A method as defined in claim 62 wherein
said radiant energy is a collimated beam of monochromatic light.

64. A method as defined in claim 62 wherein p1 said radiant energy source is a laser which produces a beam of monochromatic light.

65. A method as defined in claim 64 wherein
the identification characteristics of said known material standards are stored in a defined-storage data base, and said known material standards providing step includes automatically program controlling said generating, comparing and displaying steps.

66. A method as defined in claim 65 wherein
the defined-storage data base is on portable storage means, and the program controlling step includes operatively connecting microprocessing means to said spectrometer means.

67. A method as defined in claim 66 wherein
the portable storage means is a floppy disk or a compact disk.

* * * * *

UNITED STATES PATENT AND TRADEMARK OFFICE
CERTIFICATE OF CORRECTION

PATENT NO. : 5,017,007

DATED : May 21, 1991

INVENTOR(S) : Christopher G. Milne, et al

It is certified that error appears in the above-identified patent and that said Letters Patent is hereby corrected as shown below:

Column 5, line 5, delete "s" between "least" and "70";

Column 13, line 12, insert --11-- after "claim";

Column 13, line 36, delete "$10^{-6}$" and insert therefor, --$10^{-4}$--;

Column 14, line 14, delete "500 angstroms" and insert therefor, --3500 angstroms--;

Column 15, line 18, delete "700 angstroms" and insert therefor, --1700 angstroms--;

Column 16, line 35, delete "a" and insert therefor, -- a)--;

Column 17, line 3, delete "materials" and insert therefor, --material--;

UNITED STATES PATENT AND TRADEMARK OFFICE
CERTIFICATE OF CORRECTION

PATENT NO. : 5,017,007

DATED : May 21, 1991

INVENTOR(S) : Christopher G. Milne, et al

It is certified that error appears in the above-identified patent and that said Letters Patent is hereby corrected as shown below:

Column 17, line 9, insert --said-- after "on";

Column 18, line 9, delete "with" and insert therefor, --within--.

Column 20, line 8, delete "pl".

Signed and Sealed this

Sixteenth Day of November, 1993

Attest:

BRUCE LEHMAN

*Attesting Officer*  *Commissioner of Patents and Trademarks*